US005641486A

United States Patent [19]
Hinrichs et al.

[11] Patent Number: 5,641,486
[45] Date of Patent: Jun. 24, 1997

[54] METHODS FOR INHIBITING TRANSCRIPTION OF THE CYCLIC AMP RESPONSIVE ELEMENT BINDING PROTEIN AND THE ACTIVATING TRANSCRIPTION FACTOR 1

[75] Inventors: Steven H. Hinrichs, Omaha, Nebr.; Dana Jo Orten, Crescent, Iowa

[73] Assignee: Board of Regents of the University of Nebraska, Lincoln, Nebr.

[21] Appl. No.: 210,880

[22] Filed: Mar. 18, 1994

[51] Int. Cl.$^6$ .................................................. A61K 39/395
[52] U.S. Cl. .................................. 424/139.1; 424/145.1; 424/158.1; 530/387.9; 530/388.24; 530/389.2
[58] Field of Search ........................ 424/139.1, 145.1, 424/158.1; 435/240.1, 240.2, 236; 530/387.9, 388.24, 389.2

[56] References Cited

PUBLICATIONS

Waldman, Science, vol. 252, pp. 1657–1662 (Jun. 21, 1991).
Osband, Immunology Today, vol. 11, No. 6, pp. 193–195 (1990).
Seaver, Genetic Engineering News, vol. 14, No. 14, pp. 10 and 21 (1994).
Bach, Immunology Today, vol. 14, No. 9 pp. 421–425 (1993).
Dillman, Annals of Internal Medicine, vol. 111, No. 7, pp. 592–603 (1989).
Hai et al., Genes Dev., vol. 3, pp. 2083–2090 (1989).
Rehfuss et al., J. Biol. Chem., vol. 266, pp. 18431–18434 (1991).
Mantovani et al., EMBO J. vol. 11, pp. 3316–3322 (1992).
Sassone–Corsi et al., Cell, vol. 54, No. 4, pp. 553–560 (1988).
Zhao et al., Proc. Natl. Acad. Sci., USA, vol. 89, pp. 7070–7074 (Aug. 1992).
Campbell, Monoclonal Antibody Technology, vol. 13, Burdon et al., (ads), pp. 186–203 (1984).

*Primary Examiner*—Toni R. Scheiner
*Attorney, Agent, or Firm*—Rothwell, Figg, Ernst & Kurz

[57] ABSTRACT

The present invention relates to members of the cyclic AMP responsive element binding protein/activating transcription factor 1 (CREB/ATF1) family of transcription factors. An embodiment of this invention constitutes an inhibitory agent (e.g., an antibody, small molecule or polypeptide) which binds to a fragment, spanning from about position 167 to about 181 of the amino acid sequence of the ATF1 protein bound to the target gene, with sufficient binding affinity to cause disassociation of ATF1 from the DNA of the target gene and/or prevent ATF1 from binding thereto through a currently unknown mechanism. As a result, transcription is prevented or, at least, inhibited, resulting in events of consequence to a virus or cell.

2 Claims, 8 Drawing Sheets

SEQUENCE LISTING ( 1 ) GENERAL INFORMATION:

( i i i ) NUMBER OF SEQUENCES: 11

( 2 ) INFORMATION FOR SEQ ID NO:1:

( i ) SEQUENCE CHARACTERISTICS:
        ( A ) LENGTH: 15 amino acids
        ( B ) TYPE: amino acid
        ( C ) STRANDEDNESS: single
        ( D ) TOPOLOGY: linear     ( i i ) MOLECULE TYPE: protein     ( x i ) SEQUENCE DESCRIPTION: SEQ ID NO:1:

```
Gln  Thr  Thr  Lys  Thr  Asp  Asp  Pro  Gln  Leu  Lys  Arg  Glu  Ile  Arg
1              5                        10                       15
```

( 2 ) INFORMATION FOR SEQ ID NO:2:

( i ) SEQUENCE CHARACTERISTICS:
        ( A ) LENGTH: 27 base pairs
        ( B ) TYPE: nucleic acid
        ( C ) STRANDEDNESS: double
        ( D ) TOPOLOGY: unknown     ( i i ) MOLECULE TYPE: DNA (genomic)

( x i ) SEQUENCE DESCRIPTION: SEQ ID NO:2:

```
AGAGATTGCC TGACGTCAGA GAGCTAG                                          27
```

( 2 ) INFORMATION FOR SEQ ID NO:3:

( i ) SEQUENCE CHARACTERISTICS:
        ( A ) LENGTH: 21 base pairs
        ( B ) TYPE: nucleic acid
        ( C ) STRANDEDNESS: double
        ( D ) TOPOLOGY: unknown     ( i i ) MOLECULE TYPE: DNA (genomic)

( x i ) SEQUENCE DESCRIPTION: SEQ ID NO:3:

```
CGCTTGATGA GTCAGCCGGA A                                                21
```

( 2 ) INFORMATION FOR SEQ ID NO:4:

( i ) SEQUENCE CHARACTERISTICS:
        ( A ) LENGTH: 30 base pairs
        ( B ) TYPE: nucleic acid
        ( C ) STRANDEDNESS: unknown
        ( D ) TOPOLOGY: linear     ( i i ) MOLECULE TYPE: DNA (genomic)

( x i ) SEQUENCE DESCRIPTION: SEQ ID NO:4:

```
GACTAGATGA GAGCTACTCT AAGAGGAACG                                              30
```

(2) INFORMATION FOR SEQ ID NO:5:

(i) SEQUENCE CHARACTERISTICS:
        (A) LENGTH: 16 base pairs
        (B) TYPE: nucleic acid
        (C) STRANDEDNESS: unknown
        (D) TOPOLOGY: unknown     (ii) MOLECULE TYPE: DNA (genomic)

(xi) SEQUENCE DESCRIPTION: SEQ ID NO:5:

```
AGGGGTCAAG AGCTCA                                                             16
```

(2) INFORMATION FOR SEQ ID NO:6:

(i) SEQUENCE CHARACTERISTICS:
        (A) LENGTH: 16 base pairs
        (B) TYPE: nucleic acid
        (C) STRANDEDNESS: unknown
        (D) TOPOLOGY: unknown     (ii) MOLECULE TYPE: DNA (genomic)

(xi) SEQUENCE DESCRIPTION: SEQ ID NO:6:

```
TGGCGTCATG ACCTCG                                                             16
```

(2) INFORMATION FOR SEQ ID NO:7:

(i) SEQUENCE CHARACTERISTICS:
        (A) LENGTH: 15 amino acids
        (B) TYPE: amino acid
        (C) STRANDEDNESS: unknown
        (D) TOPOLOGY: unknown     (ii) MOLECULE TYPE: peptide     (xi) SEQUENCE DESCRIPTION: SEQ ID NO:7:

```
Thr Thr Pro Ser Ala Thr Ser Leu Pro Gln Thr Val Val Met Thr
 1               5                  10                  15
```

(2) INFORMATION FOR SEQ ID NO:8:

(i) SEQUENCE CHARACTERISTICS:
        (A) LENGTH: 15 amino acids
        (B) TYPE: amino acid
        (C) STRANDEDNESS: unknown
        (D) TOPOLOGY: unknown     (ii) MOLECULE TYPE: peptide     (xi) SEQUENCE DESCRIPTION: SEQ ID NO:8:

```
Val Val Met Thr Ser Pro Val Thr Leu Thr Ser Gln Thr Thr Lys
 1               5                  10                  15
```

(2) INFORMATION FOR SEQ ID NO:9:

(i) SEQUENCE CHARACTERISTICS:
        (A) LENGTH: 15 amino acids
        (B) TYPE: amino acid
        (C) STRANDEDNESS: unknown
        (D) TOPOLOGY: unknown     (ii) MOLECULE TYPE: peptide     (xi) SEQUENCE DESCRIPTION: SEQ ID NO:9:

```
Gln Thr Thr Lys Thr Asp Asp Pro Gln Leu Lys Arg Glu Ile Arg
 1               5                  10                  15
```

( 2 ) INFORMATION FOR SEQ ID NO:10:

( i ) SEQUENCE CHARACTERISTICS:
    ( A ) LENGTH: 20 amino acids
    ( B ) TYPE: amino acid
    ( C ) STRANDEDNESS: unknown
    ( D ) TOPOLOGY: unknown ( i i ) MOLECULE TYPE: peptide ( x i ) SEQUENCE DESCRIPTION: SEQ ID NO:10:

```
Pro  Ser  Ala  Thr  Ser  Leu  Pro  Gln  Thr  Val  Val  Met  Thr  Ser  Pro  Val
 1                    5                        10                       15
Thr  Leu  Thr  Ser
               20
```

( 2 ) INFORMATION FOR SEQ ID NO:11:

( i ) SEQUENCE CHARACTERISTICS:
    ( A ) LENGTH: 15 amino acids
    ( B ) TYPE: amino acid
    ( C ) STRANDEDNESS: unknown
    ( D ) TOPOLOGY: unknown ( i i ) MOLECULE TYPE: peptide ( x i ) SEQUENCE DESCRIPTION: SEQ ID NO:11:

```
Glu  Glu  Leu  Lys  Thr  Leu  Lys  Asp  Leu  Tyr  Ser  Asn  Lys  Ser  Val
 1                    5                        10                       15
```

METHODS FOR INHIBITING TRANSCRIPTION OF THE CYCLIC AMP RESPONSIVE ELEMENT BINDING PROTEIN AND THE ACTIVATING TRANSCRIPTION FACTOR 1

FIELD OF THE INVENTION

The present invention relates generally to members of the cyclic AMP responsive element binding protein/activating transcription factor 1 (CREB/ATF1) family of transcription factors. The consensus binding site of these sequence specific transcription factors is present in many cellular and viral promoters. Because the CREB/ATF1 family of proteins provide unique targets for cancer and antiviral therapy, the invention also relates to methods for preventing transcription factor mediated replication of cancer cells or viruses. More particularly, the present invention relates to the inactivation or inhibition of these transcription factors through binding to newly identified, specific functional domains on the transcription factor that causes dissociation from the DNA to which it is bound, preventing gene transcription. The present invention also relates generally to a method for inhibition of CREB/ATF1 family mediated gene expression and to a method for preventing transcription factor mediated viral replication or transcription factor mediated aberrant cellular proliferation. The present invention also relates to a method for detecting molecules that inhibit the binding of the CREB family of transcription factors to DNA.

BACKGROUND OF THE INVENTION

Gene expression leading to the production of protein is most frequently regulated at the level of RNA production, and is termed transcription. Generally, control of transcription is mediated by activator or repressor proteins termed transcription factors. A gene is transcribed after a sequence of events determined by transcription factors has resulted in positioning an enzyme (i.e., RNA polymerase) in the proper location and configuration on the DNA. Transcription factors act through at least two essential mechanisms: (i) binding to specific DNA sequences; or (ii) interacting with other proteins which subsequently influence transcription initiation. The DNA sequences which are involved in regulation of either viral or eukaryotic gene expression and are the targets for transcription factors occur in a variety of locations and at various distances from the transcriptional start and stop sites. These DNA sequences contributing to regulation consist of complex arrays of relatively short DNA sequence motifs. It is believed that tissue specific gene expression occurs as a consequence of cooperation between transcription factors and the DNA sequences to which they bind. Each motif is a binding site for a specific family of transcription factors.

For the CREB family, the consensus binding site has been identified by Montminy et al., 1986 Proc. Natl. Acad. Sci., USA, 83: 6682–6686). This sequence, TGACGTCA, is present in a wide variety of viral and cellular genes, most notably E1A-inducible adenoviral genes and cAMP-inducible cellular genes. Some variation is found in the core sequence with retention of essential function. Specificity of CREB protein binding to particular enhancers can be altered by interaction with viral oncoproteins, including Hepatitis B virus X (Maguire, H. F., et al, 1991, Science 252:842–844), Human T-cell leukemia virus (HTLV-1) tax (Zhao, L. J., et al, 1992, Proc. Natl. Acad. Sci. USA. 89:7070–7074; Armstrong et al., 1993, Proc. Natl. Acad. Sci. USA. 90:7303–7307; Suzuki, et al., 1993, Proc. Natl. Acad. Sci. USA. 90:610–614.; Wagner and Green, 1993, Science 262:395–399).

The CREB/ATF1 family of transcription factors is part of the bZIP superfamily of transcription factors. The most significant structural similarity is the presence of a region with many basic amino acids (b region), and a separate domain that allows close interaction with other proteins with like structure, analogous to a zipper (ZIP). The basic domain has a high concentration of the positively charged amino acids lysine and arginine, which form a tightly coiled alpha helix in the presence of DNA. The basic domain lies in close proximity to a series of amino acids in which leucine is present at every seventh position (the leucine zipper). Further, the leucine zipper forms an amphipathic alpha helix organized into coiled-coils with one surface being hydrophobic and the opposite surface being hydrophilic. This provides for close pairing or dimerization with either identical proteins (homodimers) or similar proteins (heterodimers).

The numbering of the amino acid sequences for ATF1 used in this application is based on the EuGene project designation of the ATF1—Human (fragment) reported in Entry A34223. See also Hal T. et al, Genes Dev. 3:2083–2090 (1989).

SUMMARY OF THE INVENTION

The various embodiments of this invention hereinafter discussed are based on the search for the existence of a functional domain on ATF1, a member of the CREB/ATF1 family which, when bound to a compound represented by an ATF1 specific antibody, prevents AFT1 binding to DNA. This critical domain of AFT1 has been determined to be a peptide fragment, spanning from about position 167 to about position 181 of the amino acid sequence of the ATF1 protein. This fragment is located adjacent to the DNA binding region of ATF1, and is composed of the following amino acid sequence:

Gln Thr Thr Lys Thr Asp Asp Pro Gln Leu Lys Arg Glu Ile Arg
167      170            175                      181

SEQ ID NO: 1.

Consequently, an embodiment of this invention constitutes an inhibitory agent (e.g., an antibody, small molecule or polypeptide) which binds to a fragment, spanning from about position 167 to about 181 of the amino acid sequence of the ATF1 protein bound to the target gene, with sufficient binding affinity to cause disassociation of ATF1 from the DNA of the target gene and/or prevent ATF1 from binding thereto through a currently unknown mechanism. As a result, transcription is prevented or, at least, inhibited, resulting in events of consequence to a virus or cell. It is preferred that the inhibitory agent target a region of said fragment having no more than about 8 amino acids because a smaller compound is more stable, is more capable of entering cells, and has reduced side effects.

The inhibitory compounds of this invention are further characterized by their ability to inhibit the shift or the supershift of DNA/ATF1 in the ATF Inhibition Detection Assay (AIDA) of this invention, as hereinafter more fully described. This assay provides a convenient method for the detection of compounds that bind to the target gene with sufficient binding affinity to cause disassociation of ATF1 from the DNA of the target gene.

Another aspect of the present invention relates to a method for preventing, ex vivo or in vivo, transcription factor mediated replication of cancer cells or viruses, comprising exposing said cells or viruses, ex vivo or in vivo, to an effective amount of an inhibitory agent of this invention. Said agent binds to a portion of the transcription factor, such as the region in ATF1 spanning from about position 167 to about 181 with sufficient binding affinity to cause disassociation of the transcription factor from the DNA of the target gene and thereby prevent transcription. The inhibiting compound can be an antibody, subcomponents of the antibody (e.g., Fab fragments or sFv subunits), a polypeptide representing the configuration of the antibody binding site, or small molecules that also resemble the configuration of the antibody binding site; provided that in each case the inhibiting compound is capable of binding specifically to the intended critical domain on the transcription factor (e.g., the critical domain of ATF1 previously discussed) with consequent prevention or inhibition of transcription. Another related embodiment is a method for preventing other CREB/ATF1 proteins from binding to cellular DNA, comprising exposure of said DNA to an effective amount of a compound which binds to a portion of the CREB/ATF1 proteins and prevents binding of the CREB/ATF1 proteins to DNA, preventing transcription. Especially preferred is a method for disassociating CREB/ATF1 proteins from DNA comprising exposing said DNA to an effective amount of a compound which specifically binds to a portion of mammalian CREB proteins and results in disassociation. For the CREB/ATF1 protein, ATF1, the binding domain has been determined to be SEQ ID NO: 1, representing a domain within 5 amino acids of the alpha helix DNA binding region of CREB family protiens.

Thus, a related embodiment of this invention is a method for inhibiting CREB/ATF1 family protein mediated transcription comprising exposure of the CREB/ATF1 protein bound DNA to an effective amount of a compound of this invention. The inhibitory compounds of this invention are characterized by their ability to supershift DNA/ATF1 in the ATF Inhibition Detection Assay (AIDA) of this invention, as hereinafter more fully described.

In one embodiment of this invention and, as is demonstrated hereinafter, the inhibitory compound of this invention can be a monoclonal antibody or a subcomponent of a monoclonal antibody. Exemplary of such subcomponents are Fab fragments or sFv subunits of the monoclonal antibody. The Fv element is thought to be the smallest component of an antibody that is capable of binding to the original epitope and derived sFv proteins have been shown to have binding affinities equivalent to the parent monoclonal antibody (Bird, et al, Science 242: 423–426, 1988).

Although inhibition using a monoclonal antibody (MAb), herein referred to as MAb 4, is hereinafter demonstrated, because of its size a MAb is not an ideal inhibitory therapeutic agent. Consequently, it is preferred to use the above discussed small fragments or subunits of the MAb or, alternatively, to employ a small peptide or other small molecule which binds to the ATF1 epitope depicted by Sequence No. 1. Such peptides can be detected conveniently using the AIDA assay of this invention, as is more fully described hereinafter.

DETAILED DESCRIPTION OF THE INVENTION

Examples 1–7 demonstrate the method for detecting ATF1-inhibitory compounds and inhibiting in-vitro transcription. The examples also demonstrate the use of an ATF Inhibitory Detection Assay (AIDA), as hereinafter described, to select an inhibitory compound of this invention and use of that compound to prevent transcription factor mediated replication of cancer cells.

The following preparations and methodologies are those utilized in examples 1–8.

Preparation of Recombinant CREB. Recombinant CREB was produced using CREB coding sequences, prepared according to L. J. Zhao and C. Z. Giam, Proc. Natl. Acad. Sci. USA, 89:7070–7074, 1992. The cDNA for CREB was cloned according to the methodology of Studier et al, Methods Enzymol, 185:60–89, 1990, at the NdeT/BamHI sites of the pET-11a expression plasmid. The protein was expressed from the bacteriophage T7 promoter and was purified from $Escheria\ coli$ cell lysates on DNA-cellulose columns (Sigma, Catalog # D8515).

Preparation of Recombinant ATF1. Recombinant ATF1 was produced using expression vectors containing full length ATF1, according to L. J. Zhao and C. Z. Giam, Proc. Natl. Acad. Sci. USA, 89:7070–7074, 1992. The cDNA for ATF1 was cloned according to the methodology of Studier et al, Methods Enzymol., 185:60–89, 1990, at the NcoI/BamHI sites of pET 11d. The protein was expressed from the bacteriophage T7 promoter and was purified from $Escheria\ coli$ cell lysates on DNA-cellulose columns (Sigma, Catalog # D8515).

Preparation of Nuclear Extracts. Nuclear extracts were prepared from $1-5\times10^8$ cells as described by Dignam et al., Nucleic Acids Res. 11:1475–1489, 1983, and dialyzed against 20 mM HEPES (N-[2-Hydroxyethyl]piperazine-N'-[2-ethanesulfonic acid]), pH 7.9, 100 mM KCl, 2 mM dithiothreitol, 20% glycerol, 0.2 mM EDTA (ethylenediamine tetraacetic acid), 1 mM PMSF (phenylmethylsulfonyl fluoride), 20 µg/ml aprotinin and 10 µg/ml trypsin-chymotrypsin inhibitor. Alkaline phosphatase treated nuclear proteins were prepared by digesting nuclear extracts (150 µg protein/reaction) with 20 units of calf intestine alkaline phosphatase (New England Biolabs, Catalog # 2905, 1993) in 50 mM Tris, pH 9.5, 50 mM NaCl, 5 mM $MgCl_2$ at 37° C. for 1 hr. Total protein was determined by the Bradford Assay (Biorad, Catalog # 500-0002, 1993) and amounts of ATF1 and CREB were estimated by Western blot analysis, as hereinafter described.

Preparation of monoclonal antibodies. The ATF1 monoclonal antibodies were generated using three 10 µg injections of recombinant ATF1, prepared as described above, as immunogen with the Ribi Adjuvant System (Ribi Immunochem Research Inc., Product Code # 730, Masihi, KN et. al. Int. J. Immuno Pharmacol., 8:339–345, 1989). The method used for generating the monoclonal antibodies was that of Kohler, G. and Milstein, C. (Eur. J. Immunol. 6:511–519, 1976) The panel of MAbs were screened initially by ELISA (Volker and Bidwell, *Manual of Clinical Laboratory Immunology*, 3rd Edition, Chapter 17, 1986) on plate-bound recombinant ATF1. Isotypes were determined using a kit from Amersham (Product # RPN-29). All MAb had κ light chains, MAb 1, 3 and 4 were IgG1 isotype and MAb 5 was an IgA isotype. Antibody affinity was evaluated by competitive ELISA (Friguet et al., J. Immunol. Methods, 77:605–319, 1985) using recombinant ATF1 as an antigen.

IgG1 MAb used in DNA binding and in vitro transcription assays were affinity purified on a protein G column and quantitated by spectroscopy at $A_{280}$ and the Bradford Assay (Biorad protein assay, Catalog # 500-0002). IgA antibodies in ascites fluid were quantitated by scanning IgA light chain on dried coomassie blue stained SDS-PAGE gels with a ScanMaker 600ZS (Microtek, Inc.) and analyzed using the "Image" program on a Macintosh IIci computer. This analysis determined that the MAbs IgA concentration was 10 mg/ml whereas the control was 15 mg/ml.

Anti-CREB antibody used for western blot analysis and DNA binding assays was a rabbit polyclonal antibody against the CREB α-peptide (Santa Cruz Biotechnology, Catalog # SC-58). Isotype matched myeloma proteins IgG1, κ(MOPC 15)(SIGMA), and IgA, κ(TEPC 15) were used as negative controls for the MAb assays.

Western Blot Analysis. Proteins were resolved by SDS-PAGE electrophoresis on 15% polyacrylamide gels and transferred to nitrocellulose. Nonspecific binding was blocked with 10% powdered milk in Tris buffered saline plus 0.1% TWEEN 20 and membranes were incubated for 1 hour with hybridoma tissue culture supernatants. Supernatant from each of the monoclonal cultures 1, 3, 4, and 5 were used separately and prepared in accordance with the methodologies set forth above, diluted 1:4 in Tris buffered saline. Bound antibody was detected with a commercial biotin-streptavidin-enhanced detection kit (Amersham, Product # RPN-22, 1993) used according to the manufacturer's instructions.

EXAMPLE 1

The following example demonstrates that MAb 1, 3, 4, and 5 react with untreated or alkaline phosphatase treated ATF1 on Western immunoblots of nuclear extracts from human and murine cell lines.

Immunoblotting. The MAb were tested as reagents for immunoblotting. Nuclear extracts (15 μg per lane) from HeLa human cervical epithelioid carcinoma cells (H), L929 murine connective tissue fibroblasts (L), or MT-4 HTLV-1 transformed human T cells (M) were analyzed on 15% SDS-PAGE gels with (+) or without (–) calf intestine alkaline phosphatase (Alk Phos) treatment. rC indicates purified recombinant CREB protein (15 ng per lane).

Figure 1A:
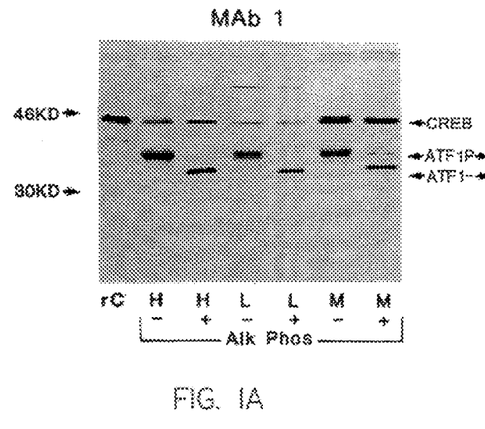
FIGS. 1A, 1B, 1C and 1D show the results of MAb 1 and MAbs 3–5 in immunoblot assays as described in Example 1. (The preparation of these MAbs is described hereinafter.)
Figure 1B:
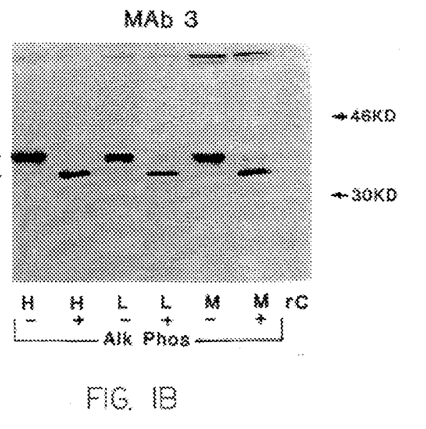
Figures 1C, 1D:
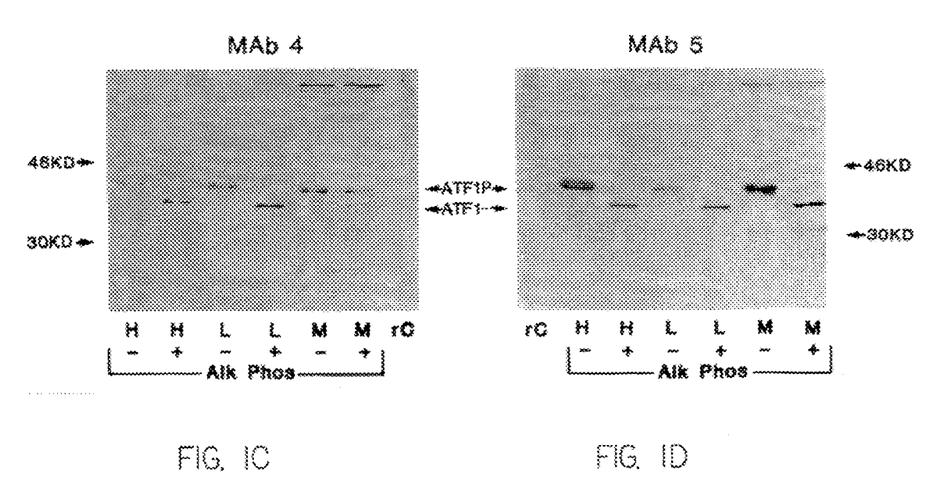
Figure 2A:
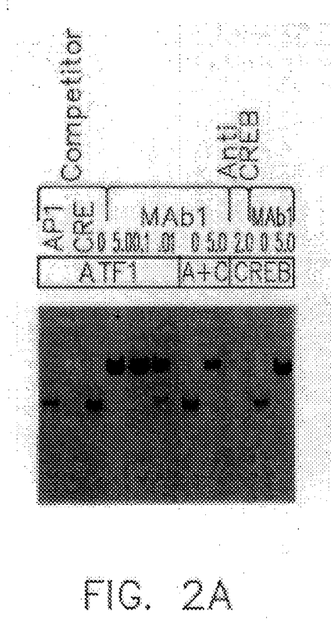
FIGS. 2A, 2B, 2C and 2D show the results of the DNA binding assay with the MAb 1 and MAbs 3–5 panel and IgA and IgG1 antibodies as described in Example 3.
Figure 2B:
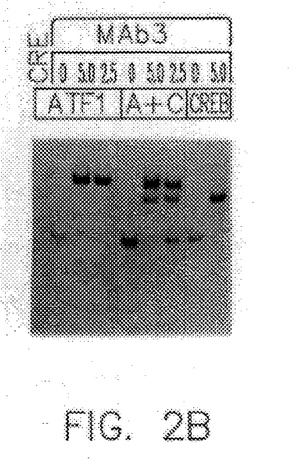
Figure 2C:
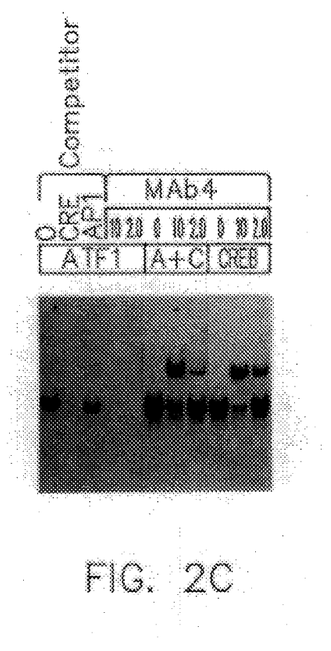
Figure 2D:
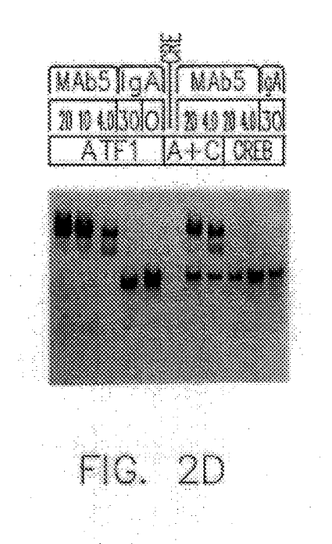

Results indicate that all 4 MAb react with untreated or alkaline phosphatase treated ATF1 on Western immunoblots of nuclear extracts from human and murine cell lines (FIG. 1). ATF1 also was readily detected in whole cell extracts from established cell lines. Only MAb 1 reacted with phosphorylated and dephosphorylated CREB in nuclear extracts. MAb 1, 3 and 5 detected as little as 0.5–1 ng of recombinant ATF1 on immunoblots; however 5–10 ng was required for reaction with MAb 4.

ATF1 INHIBITION ASSAY

ATF Inhibition Detection Assay (AIDA). Whether an antibody or compound constitues an inhibitory agent of this invention can be determined by testing the antibody or compound in the AIDA. This assay evaluates the candidate agent for its ability to inhibit ATF1 binding to DNA in the electrophoretic mobility shift assay herein referred to as the AIDA. The AIDA is generally simpler, faster, and more sensitive than other methods for detecting sequence-specific DNA-protein binding. Separate lanes of the gel are used for the following compounds respectively: 1) DNA alone; 2) DNA with ATF1; 3) DNA with ATF1 and the agent to be tested. The gels are run electrophoretically to determine which compounds result in disruption of a shift or supershift of the DNA. Larger molecules shift to a higher position on the gel and each complex produces a different and unique pattern. The use of the AIDA to identify an inhibitory agent of this invention, as exemplified by MAb4, is shown in Example 2.

EXAMPLE 2

DNA BINDING

This example demonstrates that binding of MAb4 to the novel domain (epitope) of this invention inhibits ATF1-DNA binding.

DNA Binding Assays. The double-stranded oligonucleotides used in the electrophoretic mobility shift assays, obtained from Promega were as follows: CRE: 5'-AGAGATTGCC TGACGTCA GAGAGCTAG-3' (SEQ ID #2) (CRE Catalog #E3281), AP1: 5'-CGCTTGA TGAGTCA GCCGGAA-3' (SEQ ID #3) (AP1 Catalog #E3201). DNA binding mixtures (20 μl containing 10–20 ng recombinant ATF1 and/or CREB, 1 μg poly [dI-dC], and 2.5 μg bovine serum albumin in 10 mM Tris, pH 7.5, 50 mM NaCl, 0.5 mM DTT, 0.5 mM EDTA, 1 mM $MgCl_2$, 4% (by volume) glycerol, and 0.035 picomoles $^{32}$P-labeled probe) were incubated for 20 min at room temperature, then run on native 4% polyacrylamide gels in high ionic strength buffer (25 mM Tris, 190 mM glycine, 1 mM EDTA) at 4° C.

DNA binding assays with recombinant ATF1 and CREB (FIG. 2) demonstrated that MAb 1 supershifts both ATF1 and CREB complexes to the same extent, and MAb 3 shifts CREB a lesser distance than ATF1. MAb 4 prevented ATF1-DNA binding, even if it was added after the DNA probe, but supershifted CREB. MAb 5 supershifted ATF1 and did not react with recombinant CREB.

Decreasing amounts of each MAb were used in the DNA binding assay to determine ATF1 affinity. MAb 1 has the highest affinity in this assay, with 0.020 μg of MAb (0.5:1 molar ratio of divalent antibody molecule to ATF1 monomer) completely supershifting 0.010 μg of ATF1. Two μg of MAb 3 (50:1. molar ratio) or 5 μg of MAb 5 (100:1 molar ratio) supershifted ATF1 to the slower migrating band (Supershift II) and 0.5 μg of MAb 4 (12:1 molar ratio) completely prevented 0.010 μg of ATF1 from binding to the probe. Limiting amounts of MAb 3 or 5 with ATF1 produced a faster migrating shifted band (Supershift I) at the same mobility as the MAb 1 ATF1/CREB supershift or the MAb 3 or 4 CREB supershift. Shifting all of the ATF1 to at least this level required 0.05 μg of MAb 3 (1:1 molar ratio) or 0.20 μg of MAb 5 (4:1 molar ratio).

Although not wishing to be bound by theory, it is believed that Supershift I represents one antibody molecule bound to each transcription factor dimer and Supershift II represents two molecules bound to each transcription factor dimer. A tenfold higher concentration of MAb 1 and fifty-fold higher concentrations of MAb 3 and 4 were required for CREB supershifts as compared to ATF1 supershifts or ATF1-DNA complex blocking. Reaction of MAb 3 and 4 with CREB in the DNA binding assay was surprising because these antibodies did not react with CREB on dot blots, even if CREB was pre-incubated with unlabeled CRE oligonucleotide.

Results of preliminary DNA binding experiments with HeLa cell extracts demonstrated that MAb 1, 3 and. 5 supershifted most of the CRE binding protein. MAb 3 or 5 (5–10 µg) produced two shifted complexes and a small amount of unshifted complex remained in reaction mixtures containing MAb 5. Because of the high level of ATF1 produced, most of the CREB in HeLa nuclear extracts exists as ATF1-CREB heterodimers (Hurst et al., Nucleic Acids Res., 19:4601–4609, 1991). Again not wishing to be bound by theory, it is believed the MAb 5 supershifted complexes represent ATF1 homodimers and ATF1-CREB heterodimers, and the unshifted material represents CREB-CREB homodimers. MAb 4 reduced the total amount of shifted complexes, indicating that it prevents cellular ATF1 binding and may shift or prevent heterodimer binding, depending on the relative amount of antibody and ATF1 and CREB homo- and heterodimers in the solution.

EXAMPLE 4

IN-VITRO TRANSCRIPTION

PCNA In-Vitro Transcription.

Figure 3:
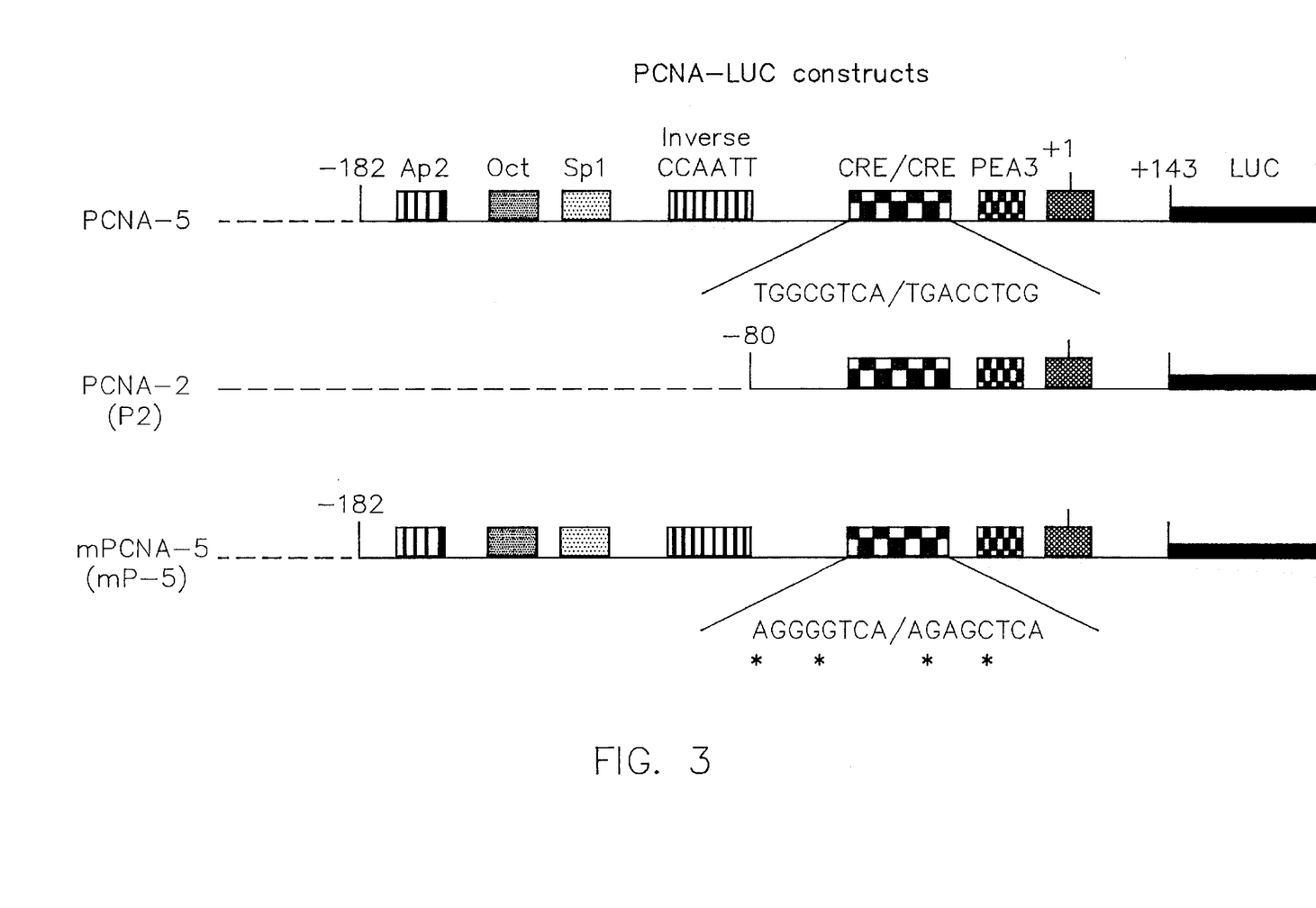
FIG. 3. Shows the promoter templates for the in-vitro PCNA transcription studies described in Example 4.

Effects of MAb on transcription were evaluated using the HeLa nuclear extract in vitro transcription system from Promega according to the manufacturer's instructions (Promega, Catalog # E3110, Protocol # TB123, 1992) except that amounts of $MgCl_2$ (5mM) and rATP (0.30 mM) were optimized as described by P. J. Farnham and R. T. Schimke (Mol. Cell. Biol., 6:2392–2401, 1986) and reactions were incubated at 26° C. for 1 hr. Antibody was incubated with nuclear extract and $MgCl_2$, for 30 min before adding rNTP's and template. Promoter templates (FIG. 3) were Proliferating Cell Nuclear Antigen (PCNA) luciferase expression vector constructs. PCNA 5 contains −182 to +143 of the PCNA promoter, including CRE/CRE, TGGCGTCA/TGACCTCG (SEQ ID #5) PCNA 2 is a truncated construct containing only the CRE/CRE and PEA3 sites (−80 to +143) and mP-5 is a PCNA-5 construct with both CRE elements mutated to AGGGGTCA/AGAGCTCA (SEQ ID #6).

Specific PCNA RNA transcription was detected using an $^{32}P$-labeled primer (5'-GACTAGATGAGAGCTACTCTAAGAGGAACG-3') (SEQ ID NO: 4) (EMBL Data Library, Accession=X53068) antisense to +97 to +127 of the PCNA gene (Shipman-Appasamy et al., DNA Seq., 2:181–191, 1991), prepared in accordance with the methodologies of Beaucage and Caruthers, Tetrahedron Letters, 22:1859–1862, 1981; and Sinha et.al., Tetrahedron Letters, 24:297–300, 1983). RNA transcripts were annealed with the primer in 10 mM Tris-HCl, pH 8, 1 mM EDTA, at 70°–75° C. for 10 minutes and cooled to room temperature for 10 minutes.

Reverse transcriptase buffer provided by the manufacturer was added and the solution was adjusted to 0.01 mM dithiothreitol, and 0.5 mM each of dATP, dTTP, dGTP, dCTP. Each 30 µl reaction was warmed to 42° C., 1 µl containing 200 units of SUPERSCRIPT™ RNase H⁻ reverse transcriptase (BRL, Catalog # 18053-017) was added, and incubated for 30 minutes. Denaturing gel buffer, 20 µl (98% formamide, 10 mM EDTA, 0.1% each xylene cyanol and bromophenyl blue) was added, samples were heated to 90° C. for 10 minutes and analyzed by electrophoresis on 6% acrylamide gels containing 7M urea in 90 mM Tris-borate, 1 mM EDTA.

The labeled 127 bp product was sized by comparison with φX174 Hinf I molecular weight markers from Promega (Catalog # E3511) and quantitated on dried gels with a Betascope 603 Blot Analyzer (Betagen Corp., Walthan, Mass., 1989) according to the manufacturer's instructions.

The effects of the panel of MAb on in vitro transcription using the murine proliferating cell nuclear antigen (PCNA) gene promoter as template were evaluated. The PCNA protein is expressed at much higher levels in proliferating cells than in quiescent cells, and is a co-factor for DNA polymerase delta, functioning in DNA replication during S phase. PCNA RNA transcription increases in interleukin-2 (IL-2) stimulated T-cells during G1 phase progression, but PCNA mRNA levels are regulated by changes in mRNA stability in serum stimulated murine 3T3 fibroblasts (Shipman-Appasamy et al., DNA Seq., 2:181–191, 1991).

Figure 4:
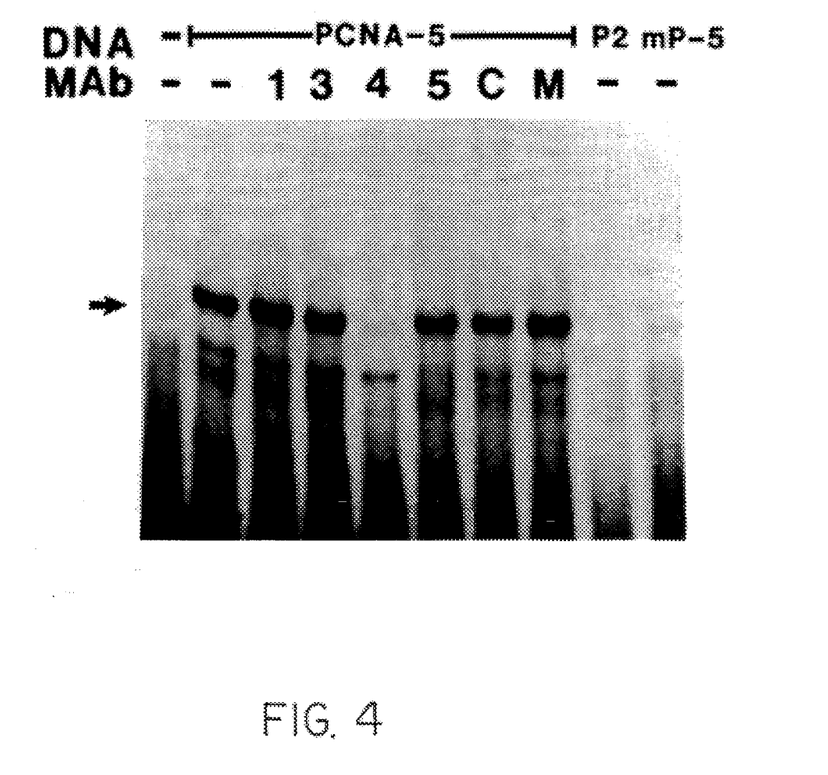
FIG. 4. Shows the effects of the MAb on in-vitro PCNA transcription as described in Example 4.

When added to HeLa cell nuclear extracts in the PCNA in vitro transcription system, MAb 4 reduced transcription to 5% of reactions with no added antibody, MAb 1 increased transcription 1.5 fold and MAb 3, 5 or control antibodies did not significantly affect transcription (FIG. 4). In preliminary experiments with murine cell nuclear extracts, MAb 4 also inhibited transcription. Transcription was reduced to 6% with a template containing mutated CRE elements, and was not detectable with a truncated template containing only CRE and PEA3 elements. Addition of MAb 4 at a approximately the same molar ratio as that required to prevent ATF1-DNA binding (12:1 molar ratio of divalent MAb to monomeric ATF1) reduced specific in vitro transcription to the same extent as mutating the CRE elements.

EXAMPLE 5

EPITOPE MAPPING

Mapping of MAb Epitope.

Because each MAb produces a different pattern in the DNA binding assay and two MAb (#1 and #4) have opposite effects on in vitro transcription, the location of the MAb epitopes within the ATF1 molecule was determined. The first step in determining the fine specificity of the MAb was to cleave recombinant ATF1 into large fragments.

Testing several enzymatic and chemical cleavage methods determined that the best results were obtained with thrombin digestion. Two major cleavage products, with apparent molecular weights on SDS-PAGE of 22 kD and 14 kD, were produced.

For MAb epitope mapping, >95% pure (by SDS-PAGE) recombinant ATF1, purified on a DNA-cellulose column, was digested for 40 or 80 hours with human thrombin (3806 NIH units/mg, Calbiochem catalog #605195) in 50 mM Tris pH 8.0, 5 mM EDTA, 1 mM dithiothreitol at 37° C., adding 0.4–1 unit of thrombin at 8–24 hour intervals. Digests were analyzed by SDS-PAGE and Western immunoblotting and major proteolytic fragments were identified by protein sequencing from electroblots as described by Matsudaira, P. (J. Biol. Chem. 262:10035–10038, 1987). The eight amino terminal amino acids of each fragment were determined and compared with the known ATF1 sequence. The 22 kD fragment contained the amino terminus of ATF1 described by Yoshimura, T., et. al. (EMBO J. 9:2537–2542, 1990) and Rehfuss, R. P., et. al. (J. Biol. Chem/266:18431–18434, 1991). The amino terminal sequence of the 14 kD fragment indicated that it was the carboxy terminal portion of ATF1 and that the major thrombin digestion site is after arginine 144 in the partial sequence described by Hai, T. et. al. (Genes and Dev. 3:2083-2090, 1989).

Immunoblotting and DNA binding analysis of thrombin-digested ATF1 indicated that MAb 1 and 3 react with the amino-terminal half of the molecule which contains domains involved in transcriptional activation (FIG. 5) and MAb 4 and 5 reacted with the carboxy-terminal half which includes the leucine zipper and DNA binding region.

Figure 6:
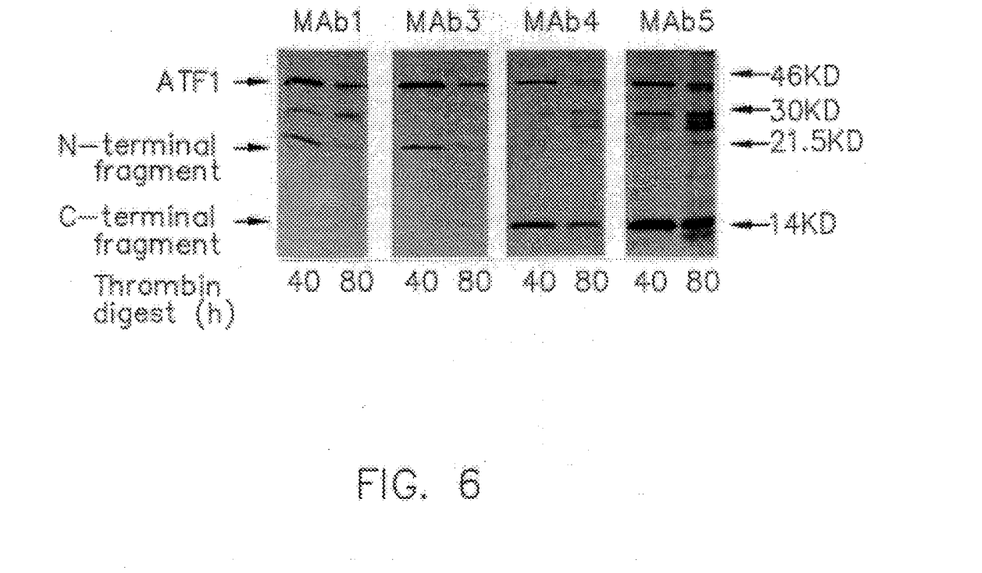
FIG. 6. Shows MAb 1 and MAbs 3–5 reactivity with major thrombin fragments of recombinant ATF1 as described hereinafter in Example 5.

MAb 1, 4, and 5 also react with a less abundant 29 kD fragment which does not react with MAb 3 (FIG. 6). This 29 kD fragment may be produced when ATF1 is digested at a consensus thrombin site within the P-box, removing 78 amino terminal amino acids. Reaction of this fragment with MAb 1 but not MAb 3 indicates that MAb 3 reacts with the amino terminal region and MAb 1, reacts with a centrally localized epitope on ATF1.

Figure 7:
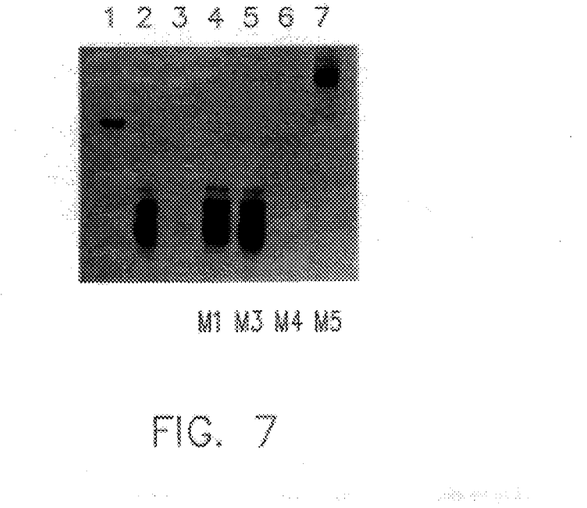
FIG. 7. Shows the DNA binding analysis with thrombin-digested ATF1: undigested ATF1 (lane 1), digested ATF1 (lane 2), digested ATF1 with 30x unlabeled CRE competitor (lane 3) or MAb 1 and MAbs 3–5 (i.e., M1 and M3–5, lanes 4–7), as described in Example 5.

Identity of the major fragments was confirmed by DNA binding analysis (FIG. 7). MAb 1 and 3 did not affect fragment-DNA bindng, MAb 4 prevented binding, and MAb 5 supershifted bound fragments. Concentrating on the shorter 14 kD DNA binding fragment, overlapping synthetic peptides were produced, representing the areas within this fragment that diverge between ATF1 and CREB.

EXAMPLE 6

PEPTIDE c REACTIVITY

MAb4 and MAb5 Reactivity with Peptide c.

Figure 5:
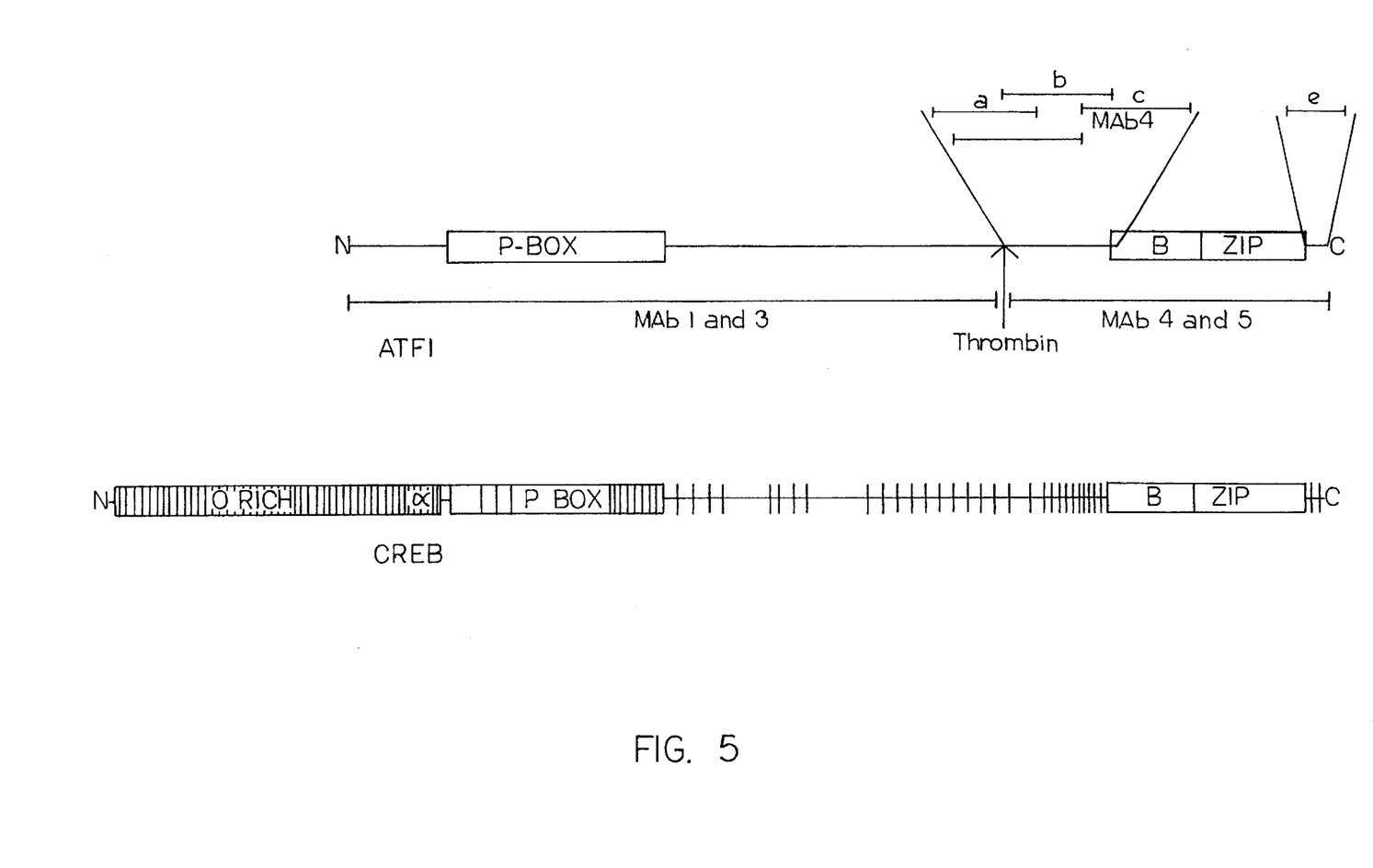
FIG. 5. Shows the regions of interest on CREB and ATF1.
Figure 8:
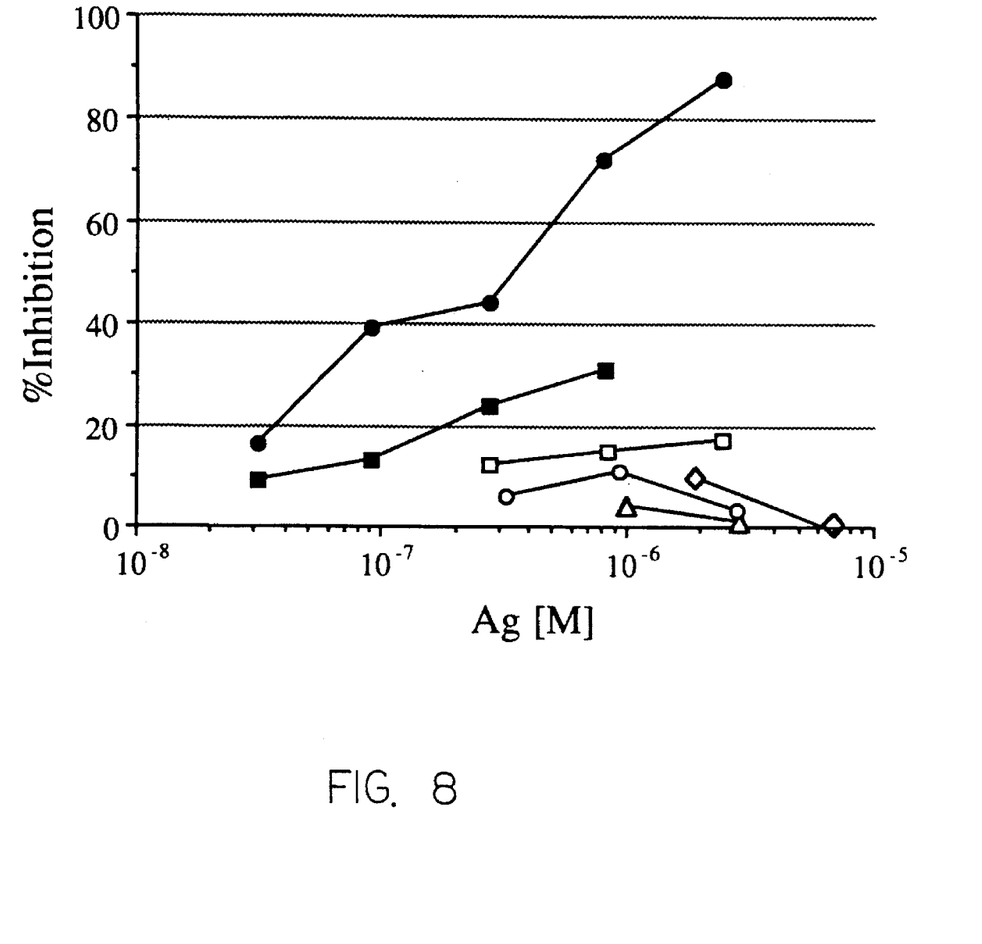
FIG. 8. Shows a graph of peptide c binding of MAb 4 by competitive inhibition ELISA as described in Example 6.

MAb 4 and 5 reactivity was analyzed by dot immunoblotting and competitive ELISA. Focusing on the shorter 14 kD DNA binding fragment which reacts with MAb 4 and 5, overlapping synthetic peptides representing the areas within this fragment that diverge between ATF1 and CREB were produced (FIG. 5). Peptides were synthesized via Fmoc procedures on a p-hydroxymethylphenoxymethyl polystyrene (HMP) resin support. After synthesis and oxidation the peptides were deprotected and cleaved from the resin by standard acidolysis in trifluoracetic acid and purified by reverse-phase HPLC methods. In FIG. 8 peptides represent the following ATF1 amino acids: a(▲):145-159 TTPSATSLPQTVVMT (SEQ ID #7); b(○): 156-170 VVMTSPVTLTSQTTK (SEQ ID #8); c(●): 167-181 QTTKTDDPQLKREIR (SEQ ID #9); d(♦): 147-166 PSATSLPQTVVMTSPVTLTS (SEQ ID #10); and e(□): 219-233 EELKTLKDLYSNKSV (SEQ ID #11). MAb 4 and. 5 reactivity was analyzed by dot immunoblotting and competitive ELISA. On the dot blots, MAb 4 reacted strongly with peptide c and MAb 5 reacted weakly with peptide d.

In the competitive ELISA, peptide c inhibited MAb 4 binding to ATF1 even more efficiently than the intact ATF1 protein (■ FIG. 8). The other peptides did not affect MAb 4 binding. None of the peptides inhibited MAb 5 binding to ATF1 in ELISA. These assays identified the MAb 4 epitope within the 10 amino acids amino proximal to the DNA binding region (amino acids 205-219, peptide c). However, although the MAb 5 epitope may be within peptide d, it is not accurately represented by the synthetic peptide and may be similar to a discontinuous epitope described by Szilvay, A. M., et.al. (Arch. Virol. 131:393-403, 1993).

From the foregoing discussion and. experimental results, it can be seen that another embodiment of the subject invention is a method for treating an individual having an ATF1-mediated disease comprising administering to said individual an effective amount of a composition selected from the group consisting of an antibody and a peptide; said composition capable of specific binding to SEQ ID NO:1 and regulating transcription, and further characterized by exhibiting a therapeutically useful change in ATF1-mediated cell behavior. The inhibitory agents of this invention are administered to said individual (e.g., a human or other mammalian host) in an amount and dosage form effective to inhibit and/or block ATF1 activity. The structures of the inhibitory agents are based on the sequence and structure of the protein target and the complementarity determining region (CDR) of the antibody which recognizes a specific domain (epitope) near the DNA binding region of the ATF1 alpha helix domain and blocks transcription. For example, as demonstrated above, the MAb 4 antibody blocks the formation of DNA-protein complexes and interferes with in-vitro transcription. Likewise, the inhibitory agents of the invention bind to the epitopic site on ATF1 and block ATF1-mediated activity. In one embodiment the inhibitory agent is composed of a peptide fragment selected or designed to bind to the essential site on ATF1.

For in vivo use the inhibitory agents of this invention are preferably administered in pharmaceutically acceptable dosage forms which contain in unit dosage form an effective amount of the inhibitory agent. In such pharmaceutically effective unit dosage forms, the inhibitory agents of this invention exhibit excellent and effective therapeutic activity in the treatment of ATF1-mediated diseases. Exemplary is the treatment of HTLV1 mediated leukemic cell proliferation. Obviously, the actual doses employed can vary and in general depend on the particular disease being treated.

A decided practical advantage is that the active inhibitory compound can be administered in a convenient manner, such as by the oral, intravenous (where water soluble), intramuscular, subcutaneous, intranasal, intradermal or suppository routes. Depending on the route of administration, the active ingredients which comprise an ATF1 inhibitory agent of this invention may be required to be coated in a material to protect said ingredients from the action of enzymes, acids and other natural conditions which may inactivate said ingredients.

In a preferred embodiment, the therapeutically effective inhibitory agent is a cyclic polypeptide containing the amino acid sequence of the complementarity determining region (CDR) of MAb 4. The CDR-containing peptide can be produced using standard techniques for isolating cDNA and expressing the peptide in standard systems and techniques from the literature. The full monoclonal antibody recognizes SEQ ID NO: 1 and the CDR derived therefrom and reconstructed as single chain recombinant polypeptide also recognizes SEQ ID NO: 1. The length of the polypeptide can be varied, provided that such variation does not negate its ability to recognize SEQ ID NO: 1. or otherwise interfere with its pharmaceutical effectiveness. In general, it is not practical for the length of the polypeptide to exceed 20 amino acid residues.

To increase the activity and solubility of the recombinant construct, the side chains of the polypeptide can be modified or pharmaceutically acceptable salts can be employed. Such side chains generally can vary in length from between about 3 to about 8 carbons.

This preferred polypeptide can be synthesized for use as either an oral solution or an intravenous solution. The preferred mode of administration is orally. Blood concentrations will vary but generally will peak between 2 and 4 hours after administration. The absolute level will be determined by the dose which is expected to range between 500 and 1400 mg/ml. The dosage is individualized based on projected blood volume or body weight of the patient. In general, a dose of between about 10 and about 20 mg/kg is effective, although higher or lower doses can be employed. When used as an antineoplastic preparation, daily dosing continues until a therapeutic regression of the tumor is seen. In cases of utilization of the therapeutic compound for treatment of inflammatory or infectious conditions, a lower dose, generally on the order of about 5 mg/kg, can generally be employed.

STATEMENT OF DEPOSIT

A deposit of the hybridoma cell line C41–4.1B disclosed above has been made with the American Type Culture Collection (ATCC), 12301 Parklawn Drive, Rockville, Md., 20852. The date of deposit was Oct. 24, 1996. All restrictions upon the deposit have been removed, and the deposit is intended to meet all of the requirements of 37 C.F.R. §1.801–1.809. The ATCC accession number is ATCC HB-12218. The deposit will be maintained in the depository for a period of 30 years, or 5 years after the last request, or for the effective life of the patent, whichever is longer, and will be replaced as necessary during that period.

We claim:

1. Method for preventing cyclic AMP responsive element binding protein family mediated replication of cancer cells or viruses comprising exposing said cells or viruses to an effective amount of an inhibitory agent which binds to a functional domain spanning from about position 167 to about 181 of the amino acid sequence of the ATF1 protein having SEQ. ID NO: 1, representing a domain within 5 amino acids of the alpha helix DNA binding region of cyclic AMP responsive element binding family proteins, with sufficient binding affinity to cause disassociation of activating transcription factor 1 from the DNA of the target gene and prevent transcription.

2. A method for treating an individual having an activating transcription factor 1 mediated disease comprising administering to said individual an effective amount of a composition selected from the group consisting of an antibody fragment, a peptide; and small molecules that resemble the spatial configuration of the paratope of an antibody that binds SEQ ID NO: 1; said composition capable of specific binding to SEQ ID NO: 1 and regulating transcription, and further characterized by exhibiting a therapeutically useful change in activating transcription factor 1 mediated cell behavior.

* * * * *